United States Patent [19]

Duranleau et al.

[11] Patent Number: 5,189,221
[45] Date of Patent: Feb. 23, 1993

[54] AMINE SEPARATION PROCESS

[75] Inventors: Roger G. Duranleau, Georgetown; Robert L. Zimmerman, Austin, both of Tex.

[73] Assignee: Texaco Chemical Company, White Plains, N.Y.

[21] Appl. No.: 617,339

[22] Filed: Nov. 19, 1990

[51] Int. Cl.$^5$ .............................................. C07C 209/86
[52] U.S. Cl. ................................... 564/499; 564/132
[58] Field of Search ......................... 564/499, 132, 291

[56] References Cited

U.S. PATENT DOCUMENTS

| | | | |
|---|---|---|---|
| 2,310,478 | 2/1943 | Tyerman | 564/499 |
| 4,510,326 | 4/1985 | Lambert, Jr. et al. | 564/132 |
| 4,529,822 | 7/1985 | Duranleau et al. | 564/132 |

Primary Examiner—Richard L. Raymond
Assistant Examiner—Shailendra Kumar
Attorney, Agent, or Firm—Jack H. Park; Kenneth R. Priem; Carl G. Ries

[57] ABSTRACT

A mixture of $C_1$–$C_4$ mono-, di- and trialkylamines is separated by adding at least about an equimolar amount, based on the amine mixture, of a formyldialkanolamine selected from the group consisting of formyldiethanolamine, formyl aminoethylethanolamine and formyl 2-(2-aminoethylamino)-ethanol to the alkyl amine mixture, at a temperature of about 120° to about 160° C. and a pressure of about 500 to about 3,000 psig to provide a reaction mixture comprising the trialkylamine, the formyl dialkylamine and the formyl monoalkylamine, together with unreacted formyldialkanolamine and the corresponding alkanolamine, by separately recovering the trialkyl amine, the formyl dialkylamine and the formyl monoalkylamine from the reaction mixture, by reacting the dialkyl amine with said alkanolamine at atmospheric pressure at temperature of about 120° to about 140° C. to provide a reaction mixture comprising the dialkyl amine and formyldialkanolamine, by recovering the dialkyl amine from the formyl reaction mixture, by separately reacting the monoalkyl amine with said alkanolamine at atmospheric pressure at a temperature of about 120° to about 140° C. to provide a reaction mixture comprising the monoalkyl amine and formyl dialkanolamine and recovering the monoalkyl amine from the reaction mixture.

16 Claims, No Drawings

AMINE SEPARATION PROCESS

BACKGROUND OF THE INVENTION

1. Technical Field of the Invention

This invention relates to a method for the purification of a mixture of alkyl amines. More particularly, this invention relates to a method for the purification of a mixture of alkyl amines prepared by the reaction of a lower aliphatic alcohol containing 1 to 4 carbon atoms with ammonia. When ammonia is reacted with the lower aliphatic alcohol, the product of the reaction is mixture of the mono-, di- and triamine derivatives of the alkanol. It is conventional practice to separate the mixture by azeotropic or extractive distillation in order to provide purified compounds.

In accordance with the present invention, a process is provided for the separation and purification of a mixture of mono-, di- and trialkylamines through the provision of a process relying upon reversible chemical reactions. In accordance with the present invention, a formyldialkanolamine selected from the group consisting of formyldiethanolamine, formyl aminoethylethanolamine and formyl 2-(2-aminoethylamino)-ethanol is added to a mixture of alkyl amines to form a reaction mixture which is heated at a temperature of about 120° to about 160° C. and at a pressure of from about 500 to about 3,000 psig to substantially quantitatively react the mono- and dialkylamines with the formyldialkanolamine to provide a reaction product comprising the trialkylamine, a formyldialkylamine, a formylmonoalkylamine, unreacted formyldialkanolamine and the corresponding dialkanolamine. The trialkylamine can be separated from the formylalkalamines by simple distillation and the formylamines can be separated from each other by vacuum distillation. Thereafter, each of the formylalkylamines is reacted with a formyldialkanolamine selected from the group consisting of formyldiethanolamine, formyl aminoethylethanolamine and formyl 2-(2-aminoethylamino)-ethanol at a temperature of about 120° to about 140° C. to provide a reaction product comprising the alkylamine and formyldialkanolamine. The alkylamine can be recovered from each of the reaction mixtures by simple distillation.

In accordance with another embodiment of the present invention, a dialkanolamine selected from the group consisting of diethanolamine, aminoethylethanolamine and 2-(2-aminoethylamino)-ethanol is brought into contact with at least an equimolar amount of carbon monoxide at a temperature of about 100° to about 200° C. and a pressure of about 700 to about 10,000 psig to substantially selectively convert the dialkanolamine to the corresponding formyldialkanolamine to form a reaction product that is useful as a starting material for the present invention, as illustrated by the following equation:

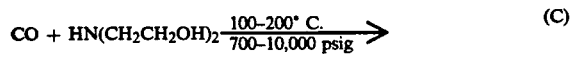

The thus prepared formyldialkanolamine is added to an alkylamine mixture and heated at a temperature of about 120° to about 160° C. and a pressure of about 500 to about 3,000 psig to form a reaction product comprising trialkylamines and formyl derivatives of the dialkylamines together with unreacted formyldialkanolamine and the corresponding alkanolamine. Thereafter, the trialkylamine, the formyldialkylamine and the formylmonoalkylamine are separately recovered by distillation. The thus separated formyldialkylamine and formylmonoalkylamine can be reacted with an additional quantity of dialkanolamine to provide the dialkylamine and the monoalkylamine and formylalkanolamine.

Prior Art

Lambert et al. U.S. Pat. No. 4,510,326 discloses a process for preparing formylalkanolamines by reacting carbon monoxide with a designated class of alkanolamines.

Duranleau et al. U.S. Pat. No. 4,529,822 discloses the preparation of formamides by reacting an amine with a formylalkanolamine in the presence of carbon monoxide.

SUMMARY OF THE INVENTION

The present invention is directed to a method for separating a mixture of alkylamines into their individual components and comprises the steps of:

a. Reacting a mixture of $C_1$-$C_4$ alkylamines, such as a mixture of methylamines, with a formyldialkanolamine selected from the group consisting of formyldiethanolamine, formyl aminoethylethanolamine and formyl 2-(2-aminoethylamino)-ethanol to provide a reaction product comprising the trialkylamine, formyldialkylamine, formylmonoalkylamine, unreacted formyldialkanolamine and the corresponding alkanolamine, b. Separately removing the trialkylamine from the reaction mixture by distillation, c. Removing the formyldialkylamine and the formylmonoalkylamine as a mixture from the reaction product by distillation, d. Separately reacting each of the formyldialkanolamine and monoalkanolamine products with an additional quantity of a formyldialkanolamine selected from the group consisting of formyldiethanolamine, formyl aminoethylethanolamine and formyl 2-(2-aminoethylamino)-ethanol to thereby generate a mixture comprising the alkylamine and a formyldialkanolamine, e. Separately recovering the dialkylamine and the monoalkylamine from their respective reaction products.

DETAILED DESCRIPTION

The starting materials for the present invention are carbon monoxide, a formyldialkanolamine selected from the group consisting of formyldiethanolamine, formyl aminoethylethanolamine and formyl 2-(2-aminoethylamino)-ethanol or, alternately, the corresponding dialkanolamine, and a mixture of $C_1$-$C_4$ alkylamines such as a mixture of methylamines, a mixture of ethylamines, a mixture of isopropylamines, a mixture of butylamines, etc.

The Formyldiethanolamine Starting Material

The formyldialkanolamine selected from the group consisting of formyldiethanolamine, formyl aminoethylethanolamine and formyl 2-(2-aminoethylamino)-ethanol starting material of the present invention may be used as such, or may be generated in situ by reacting the dialkanolamine with carbon monoxide at a temperature of about 100° to about 200° C. and a pressure of about 700 to about 10,000 psig to form a carbonylation product comprising the corresponding dialkanolamine. When this is to be done, at least one mole of carbon monoxide should be used per mole of dialkanolamine and, preferably, a significant excess of carbon monoxide should be used in order to ensure completion of the reaction of the dialkanolamine with carbon monoxide to form the formyldialkanolamine reaction product which is used as a starting material for the present invention.

The Alkylamine Starting Materials

It is conventional practice to prepare alkylamines by reacting a $C_1$–$C_4$ alcohol with ammonia over a catalyst at a high temperature. The product of the reaction is normally a mixture of all three isomers, namely, the trialkyamine, the dialkylamine and the monoalkylamine. Because the isomers will have related chemical and physical properties, they are normally separated with difficulty and are usually separated by either azeotropic distillation techniques or extractive distillation techniques.

In general, the separation process of the present invention is accomplished by mixing a mixture of alkylamines such as a mixture of methylamines with an amount of a formyldiethanolamine selected from the group consisting of formyldiethanolamine, formyl aminoethylethanolamine and formyl 2-(2-aminoethylamino)-ethanol sufficient to provide at least about 1 mole of formyldialkanolamine for each mole of primary and secondary alkylamine present in the alkylamine mixture.

The thus formed reaction mixture is then heated at a temperature of about 120° to about 160° C. and a pressure of about 500 to about 3,000 psig for about 1 to 10 hours to bring about an exchange reaction between the formyldialkanolamine and the monoalkyl and dialkylamines resulting in the formation of formylalkylamines and dialkanolamine by-product. The reactions that take place can be illustrated, for example, with respect to a mixture of methylamines as follows:

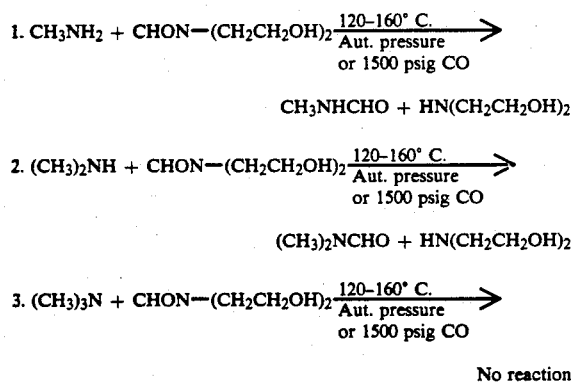

As a consequence, a reaction product is formed comprising unreacted trimethylamine, formyldialkylamine, formylmonoalkylamine, unreacted formyldiethanolamine and diethanolamine.

The trialkylamine can be separated from the reaction product by simple atmospheric pressure distillation.

In like manner, by simple atmospheric distillation a distillate fraction can be obtained comprising the formyldialkylamine and the formylmonoalkylamine.

The remainder of the reaction product, comprising unreacted formyldiethanolamine and diethanolamine can be used as a reactant in the second step of the process or can be reacted with additional carbon monoxide to form formyldiethanolamine which can be reused as a starting material.

The mixture of formyldialkylamine and formylmonoalkylamine can be separated with comparative ease by vacuum distillation into a formylmonoalkylamine fraction and a formyldiethanolamine fraction.

Each of these fractions is then reacted with diethanolamine at a temperature of about 120° to about 140° C. at atmospheric pressure for a reaction time of about 1 to 10 hours to form separate reaction products comprising the corresponding alkylamine, diethanolamine and formyldiethanolamine.

In accordance with one embodiment of the present invention, the reaction product residue from the first reaction step is used as a feed for the second reaction step being augmented, to the extent necessary, with fresh dialkanolamine in order to provide a reaction mixture comprising at least equimolar amounts of the formylalkylamine and dialkanolamine. If formyldialkanolamine is present in the initial reaction mixture, this does not present a problem if there is at least a mole of unreacted dialkanolamine present for each mole of formylalkylamine present in the reaction mixture.

At the end of the second reaction, the alkylamine is separated from the mixture of unreacted dialkanolamine and formyldialkanolamine by simple atmospheric pressure distillation. The mixture of dialkanolamine and formyldialkanolamine from this procedure can be reacted with carbon monoxide to provide formyldialkanolamine to be used as the feedback for reuse for the first step of the reaction.

SPECIFIC EXAMPLES

The invention will be illustrated by the following specific examples which are given by way of illustration and not as limitations on the scope of this invention.

EXAMPLE 1

Into a 4-liter stirred autoclave capable of accepting 10,000 psig of pressure, there was charged formyldiethanolamine (600 g=4.5 moles) along with a mixture of trimethylamine (118 g=2 moles), dimethylamine (90.0 g=2 moles) and methylamine (62 g=2.0 mole). The temperature of the constantly stirred sealed unit was brought to 155° C. and then the pressure was raised to 1500 psig with carbon monoxide. These conditions were maintained for 6 hours, then allowed to cool to room temperature while stirring overnight. The "clave" was then vented and the vent gases passed through a series of 4 dry ice traps. The off gas was sampled and found to be nearly pure CO. The trap material weighed 114 g and was >98% trimethylamine as shown by g.c. and NMR analyses. The recovery of trimethylamine was 97%. The liquid in the clave was collected (806 g formed, 864 g=theory,=93% of theory) and found to consist of a mixture of dimethylformamide, methyl formamide, formyldiethanolamine and some diethanolamine. The liquid was charged to a one-liter round bottom flask and distilled rapidly at 15 mm Hg. The liquid boiling at 72°-156° C. was collected (249 g) and redistilled at 15 mm Hg through a 12" Vigreaux column to produce two fractions boiling at 52°-55° C. and 92°-96° C. The former (137 g=94% yield) was identified as dimethyl formamide by g.c. and NMR analyses. The latter (109 g=92%) was identified as methylformamide by the same methods. The bottoms (527 g) were identified by NMR as a mixture of diethanolamine and formyldiethanolamine in a ratio 1-2.9 with a small amount of unknown impurity.

The bottoms were diluted with 2.07 moles of diethanolamine to prepare a mixture of the formyldiethanolamine and the diethanolamine in a 1/1 mole ratio (527+217 g=744 g total weight). One half of the (372 g) mixture was contacted with 73 g (1 mole) of the dimethylformamide obtained above at 140° C. for 5.5 hours. The off gases were passed through a reflux condenser maintained at 90° C. then through a series of dry ice traps (4). The liquid collected in the traps was weighed (44.0 g=98% yield) and shown to be dimethylamine by g.c. and NMR analyses. The yield of dimethylamine over all was (0.98×0.94×100=92.2%).

The second half of the mixture (372 g) was contacted with 59 g (1 mole) of the methylformamide obtained above using identical conditions. The liquid contained in the traps weighed 29 g (94%) and was shown to be methylamine by g.c. and NMR analyses. The yield of methylamine overall was (0.94×0.92=86%). The bottoms from the amine recovery are again combined and found to weigh 753 g and have an approximately 1/1 ratio of formaldiethanolamine and diethanolamine with small amounts of impurity which was unidentified.

The trimethylamine recovery was thus 97% of theory.

The dimethylamine recovery was thus 92% of theory.

The methylamine recovery was thus 86% of theory.

EXAMPLE 2

Into a 4-liter "clave" as described in Example 1 is added 945 g (9.0 moles) of diethanolamine and the "clave" is brought to 155° C. and pressured with CO at 1500 psig while stirring. These conditions are maintained until 67% (approx.) of the diethanolamine is converted to formyldiethanolamine (4-5 hours). A mixture of methylamines (270 g) consisting of 2.0 moles of each of the methylamines is added and the CO source is disconnected. The conditions (155° C. and autogenous pressure) are maintained for 4 hours then the clave is depressurized through a series of dry ice traps. The liquid in the traps is trimethylamine (112 g) recovered in 95% yield. The liquid in the clave (1274 g) is removed and distilled through a 16 inch Vigreaux column at 15 mm Hg. Pot temperatures of 140° are the maximum allowed. The overhead material (140 g) is (B.P. 52°-56° C.) dimethylformamide (96% yield). The pot is cooled and then fitted with a reflux condenser maintained at 90° C. The material is again heated at atmospheric (pot temperature is 155° C.) pressure and the escaping gas is passed through a series of dry ice traps. The trap material (59 g) is methylamine obtained in 95% yield. The bottoms (1025 g) consists of diethanolamine and formyldiethanolamine in about a 2/1 ratio.

EXAMPLE 3

Example 2 is repeated but the vacuum distillation is allowed to go to completion which produces a second fraction (B.P. 94°-98° C./15 mm Hg) weighing 110 g (93% yield). This fraction is methylformamide. The bottoms (975 g) consist of diethanolamine and formyldiethanolamine in about an 8/1 ratio.

EXAMPLE 4

In the "clave" described in Example 1 there was charged formyldiethanolamine (800 g=6.0 moles), triethylamine (202 g=2.0 moles), diethylamine (146 g=2.0 moles) and ethylamine (45 g=1.0 mole). The mixture was brought to 155° C. and the pressure raised to 1500 psig with carbon monoxide with constant stirring. These conditions were maintained for 6 hours and the clave was then cooled and vented through a dry ice trap. The trap material (20 g) was found to be unreacted triethylamine. The clave upon dismantling produced 1292 g of liquid. Total recovery was 20.0+1292=1312 g. The clave material was distilled at atmospheric pressure to produce a fraction (B.P. 90./760 mm Hg) weighing 174 g which was identified by g.c. analysis as triethylamine. Total triethylamine recovery was 174+20=194 g, corresponding to a 96% yield. The remaining liquid was then distilled at 15 mm Hg to produce two fractions B.P. 68°-70° C. (186 g) and B.P. 90°-94° C. (83 g) which were shown to be diethylformamide and ethylformamide by g.c. analysis in 92% and 83% yield respectively. The bottoms consisted of 751 g of a mixture of formyldiethanolamineand diethanolamine in about a 3/1 ratio. These bottoms were diluted with 3 moles (315 g) of diethanolamine to produce a mixture having about a 1/1 ratio of each component. A portion of this mixture (476 g) was treated with one mole of diethylformamide obtained above (101 g) and heated to 140° C. at atmospheric pressure. The evolved gas was condensed and collected as a clear liquid (139 g=95% yield) which was identified as diethylamine by g.c. analysis and comparison with an authentic sample. Another portion (350 g) of the mixture of gas treated with the 83 g of ethylformamide obtained above at identical conditions. The liquid collected (34 g=86%) was identified as ethylamine by g.c. analysis and comparison with an authentic sample.

The recovery of the ethylamines as separate fractions was therefore:
triethylamines=96% of theory
diethylamine=0.95×0.92×100=87.4% of theory
ethylamine=0.86×0.83×100=71% of theory As illustrated by the foregoing examples, the present invention provides a novel process for the separation of a mixture of alkylamines which does not rely upon azeotropic or extractive distillation.

By way of summary, light amines such as the methylamines or the ethylamines may be separated by:

1. Selective formation of the primary and secondary amine formamides,
2. Separation of the unreacted tertiary amines, primary amine formamides and secondary amine formamides usually by distillation,
3. Regeneration of the primary and secondary amine from the corresponding isolated formamide.

The first step is accomplished by contacting the mixture of amines with a formyldialkanolamine selected from the group consisting of formyldiethanolamine, formyl aminoethylethanolamine and formyl 2-(2-aminoethylamino)-ethanol to effect an exchange reaction. The reaction mixture is then distilled at ambient pressure to remove the unreacted tertiary amines as products. Further distillation at reduced pressure removes, separately, the dialkylamine formamide and the monoalkylamine formamide. The bottoms, consisting of a mixture of the alkylamine and dialkanolamine formamide are then contacted with the individual formamides at ambient pressure at pot temperatures which preclude distillation of the formamide. This regenerates the alkylamine and the formyldialkanolamine by exchange of the CO function for a second time. The following equations illustrate the process for the methylamines and formyldiethanolamine.

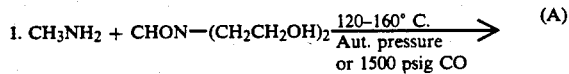

(A)

CH$_3$NHCHO + HN(CH$_2$CH$_2$OH)$_2$

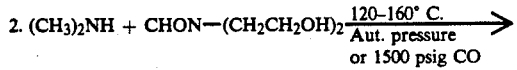

(CH$_3$)$_2$NCHO + HN(CH$_2$CH$_2$OH)$_2$

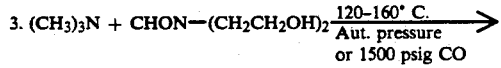

No reaction

(B)

CH$_3$NH↑ + CHON(CH$_2$CH$_2$OH)$_2$

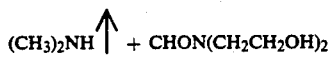

(CH$_3$)$_2$NH↑ + CHON(CH$_2$CH$_2$OH)$_2$

Separation is thus achieved for the mixture of methylamines. This method of separation has other advantages. A large portion (about 50%) of the methylamines made are eventually converted to dimethylformamide (DMF) for sale. This method of separation creates DMF as an intermediate which can be sold directly. It avoids the capital costs of a DMF plant. In this case (where DMF is sold as a product) reaction B2 will not be conducted and the bottoms will be deficient in CO. Two ways are available to regenerate the diethanolamine to formyldiethanolamine. The first is merely to conduct reaction (A) at substantial pressure of CO which regenerates the formyldiethanolamine as the formamides of the methylamines are formed. The second merely contacts the bottoms with CO at the conditions outlined above. Both cases use reaction (C) as a basis for the regeneration.

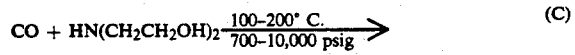 (C)

CHO—N—(CH$_2$—CH$_2$OH)$_2$

A second mode of operation is possible when DMF is a desired product. At 20 mm Hg, methylformamide boils at 102° C. while DMF boils at 50° C. When the trimethylamine has been removed from reaction mixture (A) the remainder may be adjusted to conditions which allow distillation of DMF while methylformamide remains in the bottoms. After removal of DMF and trimethylamine, methylamine may be recovered without isolating methylformamide if sufficient diethanolamine is present to allow transfer of the formyl group as in reaction B1. Such a system allows production of methyl amine, trimethylamine and DMF.

The separation scheme or schemes are equally applicable to other alkyl amine groups such as the ethyl amines. The limitation of the system is that the recovery of the formamides from reaction (A) must occur at conditions which do not cause too much loss of CO from formyldiethanolamine by reversal of reaction C. These conditions are generally confined to pot temperatures below 140° C. and pressures above 15 mm Hg. Another limitation is that the same reversal must not be appreciable during recovery of the amines as in Reaction B. Generally pot temperatures of 150° C. and pressures of 5 atm. are limiting conditions for this reaction.

Having thus described our invention, what is claimed is:

1. A method for separating a mixture of mono-, di- and trialkylamines which comprises adding at least about an equimolar amount, based on the amine mixture, of a formylalkanolamine selected from the group consisting of formyldiethanolamine, formyl aminoethylethanolamine and formyl 2-(2-aminoethylamino)-ethanol to said amine mixture and reacting the formylalkanolamine with the mono- and diamines in the amine mixture at a temperature of about 120° to about 160° C. and a pressure of about 500 to about 3,000 psig to provide a reaction mixture comprising trialkylamines, formyl alkylamines and fromyl monoalkylamines, unreacted formylalkanolamine and the corresponding alkanolamine and separately recovering the trialkyl amine, the formyl alkylamine and the formyl monoalkylamine from the reaction mixture, said alkyl amines being selected from the group consisting of C$_1$ to C$_4$ alkyl amines.

2. A method as in claim 1 wherein the dialkanolamine is diethanolamine.

3. A method as in claim 2 wherein the alkyl amines are methyl amines.

4. A method as in claim 2 wherein the alkyl amines are ethyl amines.

5. A method as in claim 2 wherein the recovered dialkyl formamide is reacted with diethanolamine at atmospheric pressure at a temperature of about 120° to about 140° C. to provide a reaction mixture comprising the dialkyl amine and formyl diethanolamine and recovering the dialkyl amine from the reaction mixture.

6. A method as in claim 5 wherein the dialkyl amine is dimethyl amine.

7. A method as in claim 5 wherein the dialkyl amine is diethyl amine.

8. A method as in claim 2 wherein the recovered monoalkyl formamide is reacted with diethanolamine at atmospheric pressure at a temperature of about 120° to about 140° C. to provide a reaction mixture comprising the monoalkyl amine and formyl diethanolamine and recovering the monoalkyl amine from the reaction mixture.

9. A method as in claim 8 wherein the monoalkyl amine is methyl amine.

10. A method as in claim 8 wherein the monoalkyl amine is ethyl amine.

11. A method which comprises the steps of:
a) bringing diethanolamine into contact with at least an equimolar amount of carbon monoxide at a temperature of about 100° to about 200° C. and a pressure of about 700 to about 10,000 psig to substantially selectively convert the diethanolamine to formyl diethanolamine,
b) adding a mixture of alkyl amines selected from the group consisting of mono-, di- and trimethyl amines and mono-, di- and triethyl amines to the formyldiethanolamine at a temperature of about 120° to about 160° C. and a pressure of about 500 to about 3,000 psig to form a reaction product comprising the formyl derivatives of the dialkyl amine and of the monoalkyl amines contained in the amine mixture, and unreacted formyl diethanolamine and diethanolamine, c) separately recovering the trialkyl amine, the formyl dialkylamine and the formyl monoalkyl amine from the reaction product.

12. A method as in claim 11 wherein the alkyl amines are methyl amines.

13. A method as in claim 11 wherein the alkyl amines are ethyl amines.

14. A method as in claim 11 wherein formyl diethanolamine is added to the mixture of diethanolamine and formyl diethanolamine remaining after removal of the trialkyl amine and the di- and mono alkyl formyl amines in an amount sufficient to provide about an equimolar mixture of the diethanolamine with the formyl diethanolamine and wherein at least a portion of the recovered formyl dialkyl amine is added to at least a portion of the said equimolar mixture of the diethanolamine with the formyl diethanolamine at atmospheric pressure at a temperature of about 120° to about 140° C. to provide a reaction mixture comprising the dialkyl amine, diethanolamine and formyl diethanolamine, and recovering the dialkyl amine from the reaction mixture.

15. A method as in claim 14 wherein the dialkyl amine is dimethyl amine.

16. A method as in claim 14 wherein the dialkyl amine is diethyl amine.

* * * * *